United States Patent [19]

Danforth

[11] Patent Number: 4,881,547

[45] Date of Patent: Nov. 21, 1989

[54] ANGIOPLASTY DILITATION BALLOON CATHETER

[76] Inventor: John W. Danforth, 875 25th Ave., San Francisco, Calif. 94121

[21] Appl. No.: 239,061

[22] Filed: Sep. 1, 1988

Related U.S. Application Data

[63] Continuation-in-part of Ser. No. 91,689, Aug. 31, 1987, abandoned.

[51] Int. Cl.$^4$ ............................................. A61M 29/02
[52] U.S. Cl. ..................................... 128/344; 604/101; 604/53
[58] Field of Search .................... 128/344; 604/101, 53

[56] References Cited

U.S. PATENT DOCUMENTS

| | | | |
|---|---|---|---|
| 4,467,790 | 8/1984 | Schiff | 128/344 |
| 4,582,181 | 4/1986 | Samson | 128/348 |
| 4,644,936 | 2/1987 | Schiff | 128/344 |
| 4,646,742 | 3/1987 | Packard et al. | 128/344 |
| 4,684,363 | 8/1987 | Ari et al. | 604/98 |

FOREIGN PATENT DOCUMENTS 0228787  7/1987  European Pat. Off. .

OTHER PUBLICATIONS

WO8606285 Crittenden, Nov. 1986.

*Primary Examiner*—E. Rollins Cross
*Attorney, Agent, or Firm*—Townsend and Townsend

[57] ABSTRACT

A dilitation balloon catheter with an inelastic balloon disposed in a streamlined configuration having a smaller deflated cross-sectional profile than any catheter hereto available and yet a potentially larger inflation caliber than prior art "low profile" catheters. During introduction across a region of stenosis, the balloon is wrapped around a guidewire in such a way that the guidewire contained therein can move freely. The wrapped configuration is maintained by means of a temporary bond. Inflation of the balloon, following proper positioning of the catheter results in disruption of the aforementioned bond, permitting a balloon to unwrap from the guidewire contained therein.

33 Claims, 7 Drawing Sheets

FIG._2B. (PRIOR ART)
INFLATED

FIG._2C.
(PRIOR ART)
DEFLATED

ANGIOPLASTY DILITATION BALLOON CATHETER

This application is a file wrapper continuing continuation-in-part of application serial number 07/091,689, filed Aug. 31, 1987, now abandoned.

BACKGROUND OF THE INVENTION

1. Field of the Invention

This invention relates to catheters, and in particular to dilitation balloon catheters, for use in the performance of percutaneous transluminal procedures including peripheral angioplasty, coronary angioplasty and valvuloplasty. The configuration of the catheter permits the introduction of a relatively large caliber balloon across a severe intraluminal stenosis with relative facility.

2. Description of the Prior Art

In 1977 Dr. Andreas Greüntzig first used a balloon-tipped flexible catheter to percutaneously dilate a region of stenosis within a coronary artery of a patient with atherosclerotic heart disease. Since that time, the incidence of percutaneous transluminal coronary angioplasty has increased exponentially. Over the course of the past three to four years, the performance of this procedure has become routine within many major medical centers throughout the world. With the advent of improved technology and operator skill, the indications for this procedure have also increased substantially.

At the outset of a routine percutaneous transluminal coronary angioplasty procedure, a preshaped angioplasty guiding catheter containing a balloon catheter equipped with a flexible intracoronary guidewire is engaged within the ostium of a coronary vessel containing the lesion to be dilitated. Once suitably engaged (within the left main or right coronary ostium), the guidewire is advanced within the lumen of the appropriate vessel and manipulated across the region of stenosis. By rotating the guidewire, which contains a slight bend within its distal aspect, the operator can control the course of the wire, selecting the appropriate coronary lumen as the wire is advanced.

Once the wire is positioned across the region of stenosis (narrowing), the angioplasty dilitation balloon catheter is advanced over the guidewire and positioned across the stenotic lesion. The angioplasty is accomplished by inflating the dilitation catheter to a high pressure, typically 6 to 10 atmospheres. Generally, 3 to 4 dilitations are required for each region of stenosis. Balloon inflation is maintained for 30 to 90 seconds during each dilitation, depending upon anatomic considerations and operator preference.

Following the final dilitation, the guidewire and balloon catheter are withdrawn leaving the guiding catheter in place. (Frequently, an exchange wire is installed within the lumen of the coronary artery via the guiding catheter prior to removal of the balloon catheter. This ensures intraluminal access in the event of a complication.) Selective coronary angiography then is performed to evaluate the cosmetic appearance of the vessel following the angioplasty and to determine the severity of the residual stenosis.

Figure 1A:
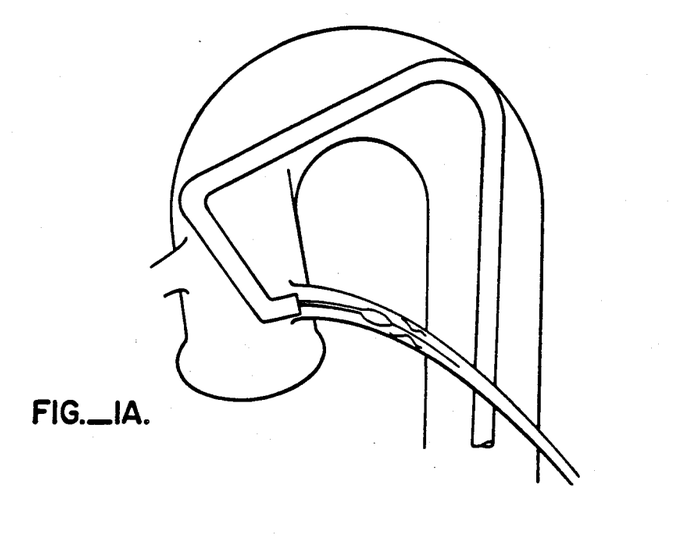
FIG. 1A is a schematic diagram illustrating the normal configuration of a Judkin's guiding catheter within the aorta following engagement with the ostium of the left main coronary artery and introduction of a dilitation balloon catheter over an intracoronary guidewire to within the proximity of a lesion contained within the left anterior descending coronary artery.
Figure 1B:
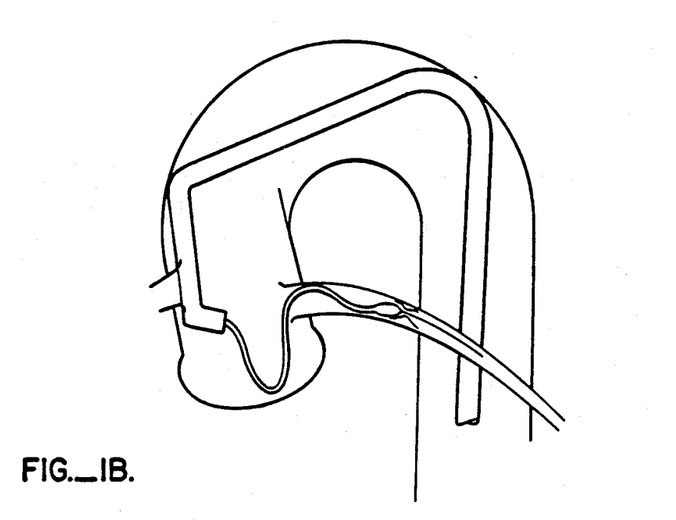
FIG. 1B illustrates the distortion in the configuration of the guiding catheter that frequently results from attempts to advance a dilitation catheter across a stenosis.

At present, the major obstacle to the performance of an angioplasty procedure involves the manipulation of the angioplasty dilitation balloon catheter across the region of stenosis within the coronary artery. Although the guidewire can frequently be advanced across the region of stenosis with relative facility in vessels which are anatomically amenable to the performance of an angioplasty (see FIG. 1A), manipulation of the balloon catheter across the stenosis often proves difficult because the cross-sectional profile of the deflated balloon affixed to the distal aspect of the dilitation catheter is considerably greater than the corresponding profile of the intracoronary guidewire. Advancing the relatively large caliber angioplasty catheter within a significant stenosis commonly results in disengagement of the guiding catheter from the coronary ostium. Once the guiding catheter becomes disengaged, the angioplasty catheter frequently prolapses within the sinus of Valsalva immediately cephaled to the aortic valve, precluding further advancement of the angioplasty catheter (see FIG. 1B). The guiding catheter disengages in this circumstance because it is moderately flexible. It must be flexible because insertion of this catheter requires that it be advanced over a guidewire up the aorta, which is relatively straight, and then over the aortic arch, which is, as the name implies, curvilinear.

One approach to circumvent this problem involves the development of angioplasty dilitation balloon catheters that impart less resistance during manipulation across a coronary stenosis relative to conventional profile dilitation catheters. The approach to the development of these angioplasty catheters has, in essence, involved the miniaturization of conventional balloon catheters. These "low profile" catheters have substantially contributed to the feasibility of performing angioplasty individuals with severe coronary stenoses previously considered unsuitable for percutaneous transluminal coronary angioplasty.

FIG. 2 illustrates the basic configuration of a conventional angioplasty balloon catheter. The catheter consists of a lumen to accommodate a guidewire, an inflation channel, as well as a small dilitation balloon affixed to the distal aspect. Attempts to miniaturize these conventional catheter systems has resulted in several disadvantages, given the constraints imposed by current technology and material availability. For example, the balloons of these "low profile" systems tend to have a correspondingly smaller inflated diameter relative to conventional balloons. This circumstance derives from the fact that the most suitable material for the construction of dilitation balloons must be relatively inelastic. Thus, the use of these "low profile" catheters frequently obligates the operator to install one or more dilitation balloon catheters of sequentially larger caliber. In addition to the added expense, radiation exposure and operative time that this approach involves, the complication rate for an intravascular procedure is in direct proportion to the number of catheters employed during the procedure, as well as the time required to complete the operation.

Despite extensive research and development, the deflated profile of these "low profile" catheters remains substantial, hence the resistance imparted by these devices during manipulation within a coronary stenosis remains considerable. Furthermore, the introduction of a "low profile" catheter of conventional configuration within a region of stenosis commonly deforms the deflated balloon resulting in the development of wrinkles which further contribute to the resistance generated by the catheter (see FIGS. 2C and 2D).

To circumvent the problems intrinsic to miniaturizing the balloon component of the catheter, the Hartzler system was developed wherein the caliber of the guidewire was reduced relative to the other components of the system. Because this results in a fragile guidewire, the system was designed such that the guidewire could not be removed from the protective confines of the dilatation balloon catheter lumen. Disadvantages of this system include the inability to accommodate conventional guidewires that afford relatively superior directional control and the maintenance of a guidewire within the coronary artery during the process of exchanging dilatation balloon catheters.

The configuration of the Hartzler system does permit rotation of the guidewire about the axis of the catheter and this feature affords some, albeit suboptimal, directional control to the catheter system. The configuration of the Hartzler system, however, does not permit (1) 360° rotation of the guidewire, and (2) independent movement of the guidewire relative to the catheter along the axis of the system. Because the caliber of the Hartzler balloon is relatively small, when fully inflated, use of this device frequently mitigates the use of one or more subsequent dilitation balloon catheters of sequentially larger caliber in order to achieve an optimal result. Because the Hartzler system does not accommodate an exchange wire, the operator must completely renegotiate the course of the diseased coronary artery with another intracoronary guidewire before advancing the subsequent larger caliber angioplasty dilitation balloon catheter across the region of stenosis. This inability to use an exchange wire enhances the difficulty of the procedure and thus predisposes the patient to increased risk. Many operators prefer to install an exchange wire within a coronary artery during the process of exchanging dilitation balloon catheters to ensure intraluminal access in the event that a complication occurs during the process. The use of the Hartzler system does not permit this.

Although conventional "low profile" catheter systems can accommodate an exchange wire, there exist some intrinsic disadvantages to these catheter systems relative to the Hartzler system. The deflated profile of conventional low profile systems tends to exceed the corresponding profile of the Hartzler system. Hence, it is frequently more difficult to advance one of the these catheters across a region of critical stenosis relative to the Hartzler system. Secondly, the lumen of low profile catheters cannot accommodate the larger caliber intracoronary guidewires. Given the fact that torque control and hence, directional control are directly related to the caliber of the guidewire, the use of conventional low profile catheter systems requires the use of guidewires with suboptimal directional control. This feature further limits the likelihood of success in the performance of an angioplasty of a complete coronary occlusion (wherein the use of a low profile catheter system would be optimal). Most operators prefer to use relatively large caliber (0.018 inch) intracoronary guidewires in the performance of an angioplasty of a complete coronary occlusion because of the enhanced column strength that this increased caliber affords, and small caliber guidewires tend to buckle in this circumstance. While one would prefer to use a low profile system in this situation, the fact that these systems do not accommodate a stiff wire tends to mitigate against their use in this circumstance.

SUMMARY OF THE INVENTION

The angioplasty dilitation balloon catheter of the preferred embodiment of my invention provides numerous advantages relative to prior art catheters. In particular, the configuration of the catheter permits the introduction of a relatively large caliber balloon across a severe stenosis with relative facility by maximizing the ratio of the inflated balloon cross-sectional profile to the corresponding deflated profile of the distal dilitation balloon. Relative to prior art dilitation catheters, the distal deflated profile is considerably smaller. As a result, the resistance imparted by the balloon during catheter manipulation within a coronary is considerably less than the corresponding resistance of prior art "low profile" catheters, yet the inflated caliber of the balloon is substantially greater than the corresponding profile of conventional "low profile" catheters. Thus, the use of this catheter frequently eliminates the need to install exchange wires, and subsequent larger caliber dilitation catheters, thus precluding the complications associated with these additional procedures. As a result, use of this device substantially contributes to the efficiency and safety of performing an intraluminal dilitation procedure (e.g., peripheral angioplasty, coronary angioplasty, valvuloplasty, ureteral stenosis dilitation, etc.).

In a preferred embodiment, the catheter includes an inflatable balloon disposed on the distal aspect of the catheter, a channel to accommodate a guidewire, extending from the proximal end to the balloon, and a means to inflate the balloon. Typically, the balloon is wrapped around the guidewire, thus forming a channel to accommodate the guidewire contained therein. This wrapped configuration affords several advantages. It provides a very compact streamlined means for disposing the balloon in the deflated state that permits the maximization of the balloon cross-sectional inflation/deflation profile ratio while circumventing the use of elastic elements in the construction of the balloon to accomplish this end.

Figure 2A:
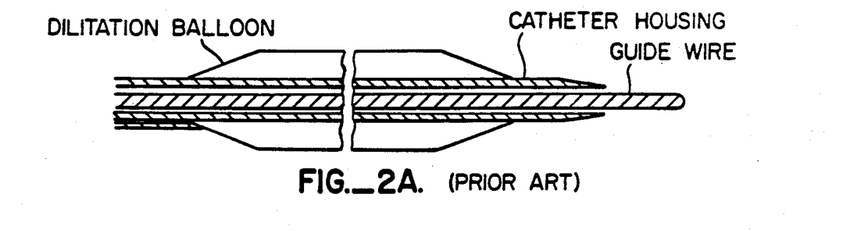
FIG. 2A is a cross-sectional side view of a conventional prior art angioplasty dilitation balloon catheter.
Figure 2B:
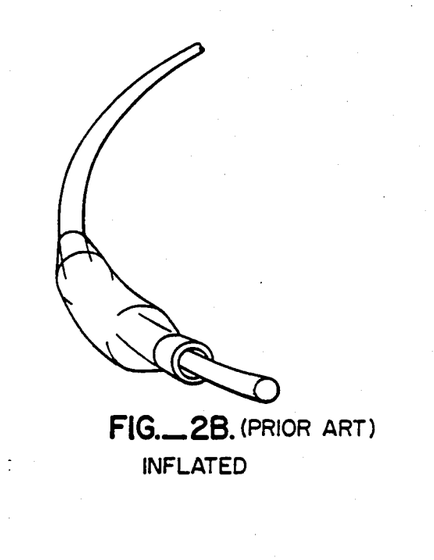
FIG. 2B illustrates the prior art catheter fully inflated.
Figure 2C:
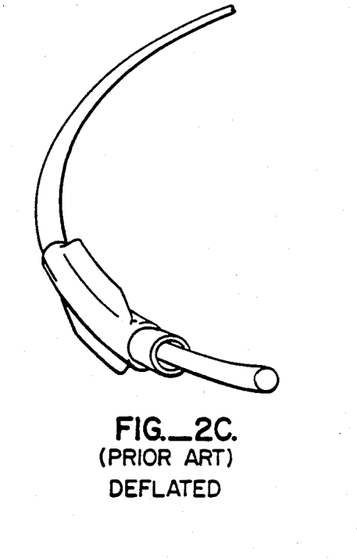
FIG. 2C illustrates the catheter when deflated.
Figure 2D:
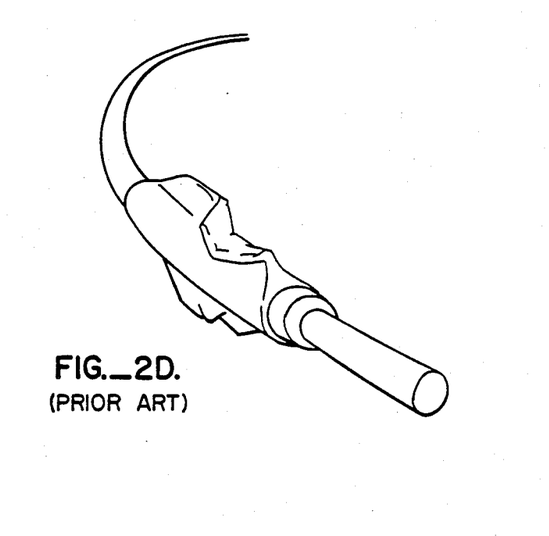
FIG. 2D illustrates the development of wrinkles within the deflated balloon of the prior art consequent with introduction of the dilitation catheter across a region of stenosis.

The wrapped balloon configuration permits considerable reduction in the deflated cross section balloon profile relative to the corresponding profile of prior art catheters because this configuration (1) precludes the development of flanges within the balloon itself that extend radially from the distal aspect of the catheter (see FIG. 2C); (2) precludes the development of wrinkles at the junction of the balloon and guidewire housing; (3) precludes the development of wrinkles within the flanges of the balloon during manipulation of the catheter across a stenosis (see FIG. 3B); and (4) eliminates the bulk intrinsic to the bond of the balloon to the guidewire housing that contribute to the deflated profile of the prior art catheters.

The wrapped configuration further imparts column strength to the balloon, thus eliminating the need to extend the guidewire catheter housing within the confines of the balloon. This permits further reduction in the deflated cross-sectional balloon profile of the catheter of my design. The wrapped balloon configuration has particular application to the performance of valvulopasty. In this circumstance, this configuration permits the introduction of a relatively large caliber balloon (requisite to the performance of a valvuloplasty) within the vasculature via a relatively small arteriotomy of hematomas, hemophage, and peripheral arterial trauma that frequently complicate conventional valvuloplasty procedures. Furthermore, the wrapped configuration permits the introduction of a large caliber balloon within the heart without the risk of inducing intracardial trauma consequent with balloon inflation (a problem intrinsic to dilitation balloon catheters of the prior art) because the distal aspect of the balloon becomes blunt on full inflation (see FIG. 4D).

DETAILED DESCRIPTION OF THE PREFERRED EMBODIMENTS

Although it is acknowledged at the outset that the configuration of the catheter described herein has application to the performance of a variety of dilitation procedures including peripheral angioplasty, valvuloplasty and dilitation of ureteral stenosis. For the purpose of clarity, the balance of the text will be confined to a discussion of the application of this device to the performance of percutaneous transluminal coronary angioplasty.

Figure 3:
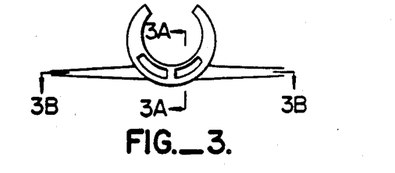
FIGS. 3, 3A, 3B, and 3C are side, top and end views of a preferred embodiment of the catheter.
Figure 3A:
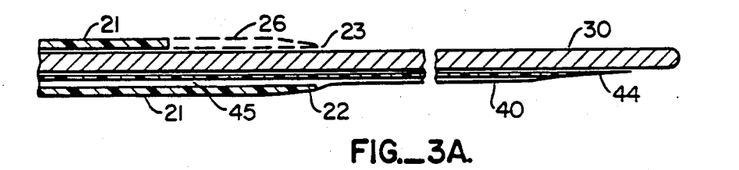
Figure 3B:
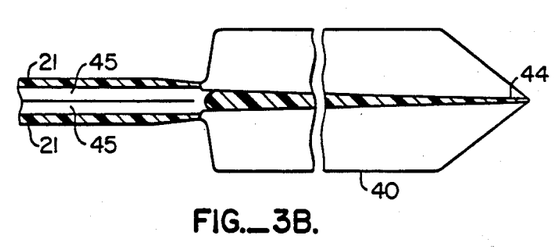
Figure 3C:
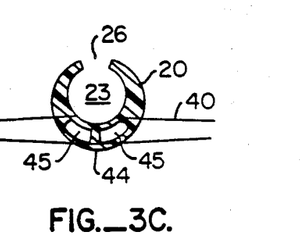

FIGS. 3A, 3B and 3C are a longitudinal sectional, top and end view, respectively, of the cutaway angioplasty dilitation balloon catheter of a preferred embodiment of my invention. An inset has been provided for the purpose of orientation with respect to FIG. 3A. A guidewire has been included in FIGS. 3A and 3E for orientation. As shown in FIG. 3, the catheter includes a housing 21 extending from a proximal end (not shown) to a distal end 22 creating a lumen 23 to accommodate an intracoronary guidewire 30. The balloon typically is formed from an inelastic material so it will inflate uniformly to a predetermined configuration.

FIG. 3B illustrates the housing 21, communicating channels 45, and balloon 40 from above. The balloon is shown in an unwrapped deflated condition. FIG. 3B also illustrates an optional feature of the catheter, specifically, a stiffening element 44 disposed longitudinally along the length of the balloon to provide additional column strength to the balloon. FIG. 3C is a "phantom" end view of the catheter illustrating the disposition of channels 45 within the confines of the catheter housing. The communicating channels 45 provide a means for both flushing air out of the catheter prior to introduction into the body as well as inflating the dilitation balloon 40 once the catheter has been positioned across a region of stenosis.

Figures 3D, 3E:
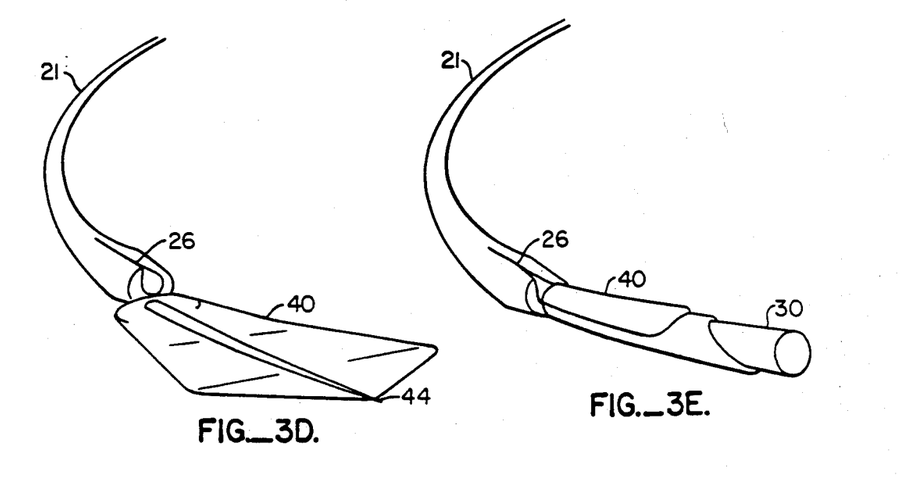
FIG. 3D illustrates the catheter in perspective view with the dilitation balloon unwrapped.
FIG. 3E is a perspective view of the catheter with the dilitation balloon wrapped around an intracoronary guidewire.

FIG. 3D is a perspective view of the dilitation balloon 40, in an unwrapped deflated condition and optional stiffening element 44. For clarity, guidewire 30 is not shown in FIG. 3D. FIG. 3E is a perspective view of the dilitation balloon 40 and guidewire 30 illustrating the manner in which the dilitation balloon may be wrapped around the guidewire. Relative to prior art catheters, this configuration permits the disposition of a relatively large inelastic balloon along the course of a guidewire with a minimal cross-sectional profile. (The guidewire is shown larger than to scale for illustration.) Typically, the balloon will be wrapped around the guidewire at the time of manufacture and will not be unwrapped until it is inflated within the region of the stenosis. Both the lumen 23 in housing 20 and the lumen created by wrapping balloon 40 are of sufficient caliber to permit unimpaired longitudinal and rotational movement of guidewire 30 within the confines of the catheter. Notwithstanding the small insertion diameter, on inflation, the balloon unwraps from the guidewire and provides the full capability of existing angioplasty dilitation balloons. A slot 26 at the end of the housing 21 allows the balloon to be inflated near the end of housing 21 without unduly stressing the guidewire 30. The configuration of the balloon 40 can be modified to optimize the taper that develops along the leading edge of the catheter on wrapping the balloon around the guidewire as illustrated in FIG. 3E.

Because the balloons used in the construction of conventional catheters have very thin walls, the wrapping of a relatively large balloon around a guidewire does not lead to a significant increase in the overall deflated cross-sectional diameter of the catheter relative to the corresponding profile of a catheter containing a smaller caliber dilitation balloon. Hence, this configuration of the preferred embodiment provides a catheter of lower deflated profile that contains a relatively larger balloon than prior art catheters. Because the use of the catheter described herein permits the initial introduction of a balloon of optimal caliber within a severe stenosis with minimal resistance (relative to conventional prior art low-profile catheters), without the need to introduce and inflate several additional dilitation catheters across the region of stenosis the use of this system reduces the difficulty, expense, duration, and risk of the dilitation procedure. Because the catheter readily accommodates 0.018 inch (large caliber) guidewires and exchange wires, the use of this catheter does not compromise directional control for miniaturization as do currently available low profile systems. Furthermore, the catheter permits the maintenance of a previously installed exchange wire within the coronary artery following balloon dilatation in the event that the operator desires to maintain intraluminal access, an option not feasible with the Hartzler system. For all of these reasons, the use of my catheter enhances the safety, feasibility, efficiency and economy of an intraluminal dilitation procedure.

To provide additional column strength to manipulate the catheter across a tight stenosis, the lumen of the balloon may be made smaller than the guidewire lumen of the catheter housing. In this circumstance, a tapered guidewire allows the operator to manipulate the balloon across the stenosis by applying pressure to the guidewire itself. In this circumstance, the column strength of the guidewire contributes to the column strength of the catheter. On inflation of the balloon, the guidewire and catheter part. The addition of an optional stiffener 44, as illustrated in FIGS. 3A, 3B and 3D contributes to the column strength of the balloon.

Figures 4A, 4B:
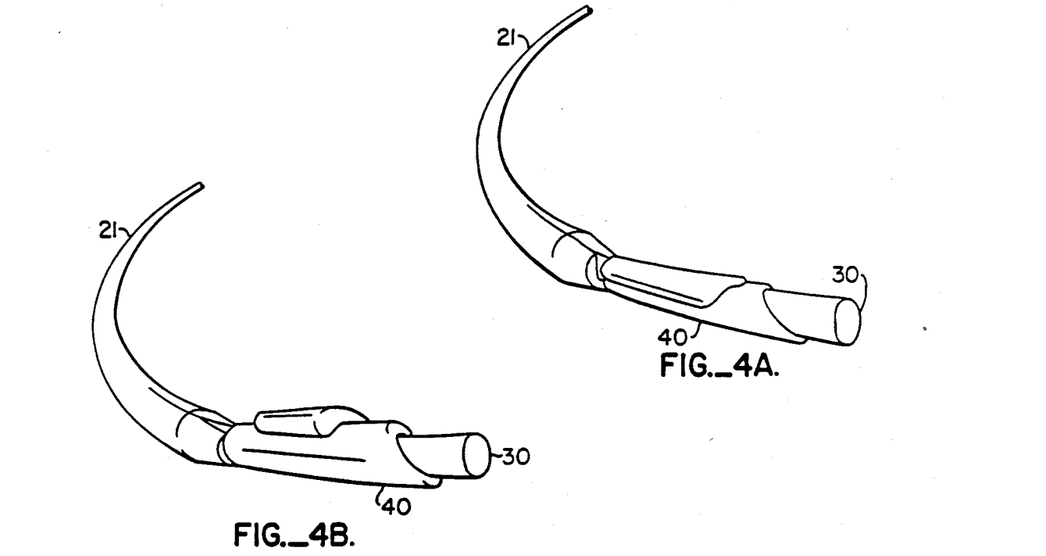
FIGS. 4A–4D are a sequence of views illustrating the inflation of the dilitation balloon.
Figure 4C:
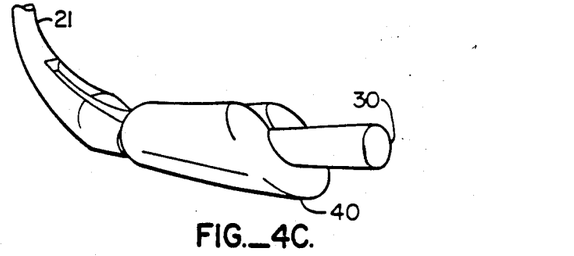
Figure 4D:
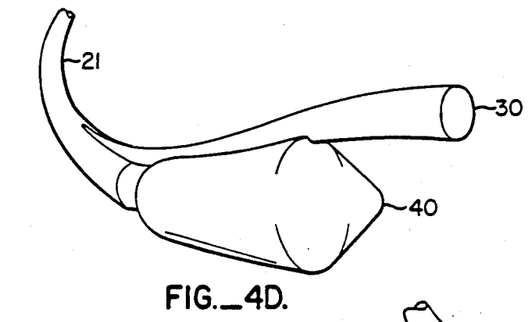

FIGS. 4A-4D illustrate the manner in which the wrapped balloon unwraps during inflation. When first manipulated across a stenosis, balloon 40 is wrapped in the manner of FIG. 4A. This configuration is maintained by a temporary bond designed to tolerate the stresses usually applied to this segment of the catheter during introduction across a coronary stenosis and yet release when subjected to the forces that develop during inflation of the balloon. This bonding may be achieved using any well known technique including, for example, ultrasonic bonding. As shown in FIGS. 4B and 4C, as the balloon is progressively inflated by fluid inserted through the channels, the bond (or bonds) breaks, allowing the balloon to unwrap from the guidewire 30. Once it is completely unwrapped, as shown in FIG. 4D, the guidewire is no longer encompassed by the balloon.

Figure 4E:
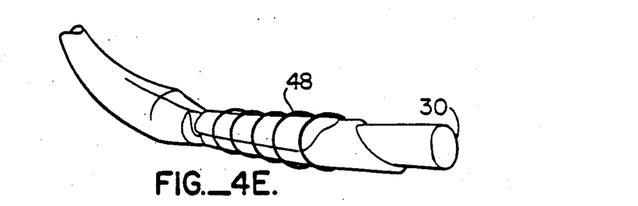
FIG. 4E illustrates a catheter with a stint encompassing the deflated wrapped dilitation balloon.

In an alternate embodiment shown in FIG. 4E, a stint 48 is used to maintain the balloon 40 in a wrapped position. When the balloon 40 is inflated, the stint 48 is deformed to an enlarged shape and remains within the artery to hold the lumen open. Thus, the catheter functions as an optimal device to introduce stints into the vasculature.

Figure 5A:
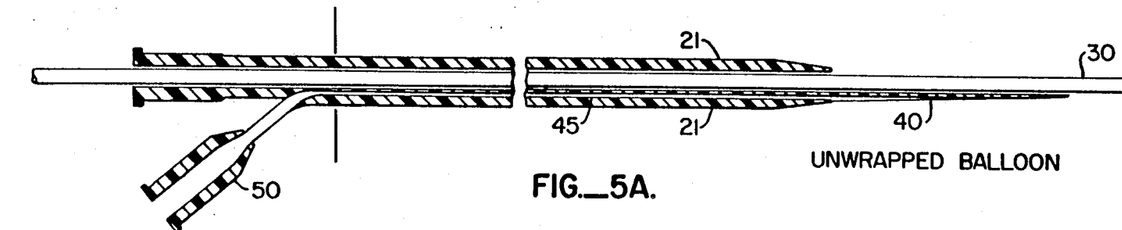
FIGS. 5A–5C illustrate three different embodiments of the catheter in which the guidewire housing is changed.
Figure 5B:
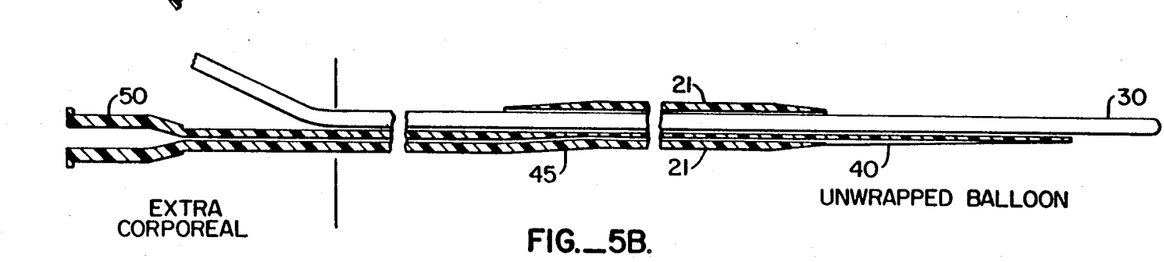
Figure 5C:
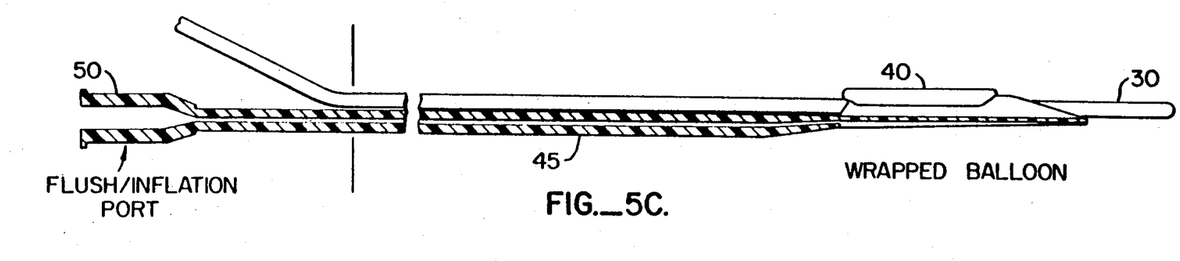

FIGS. 5A, 5B and 5C illustrate three different embodiments for the design of the housing 20 of the catheter. In FIG. 5A, the guidewire 30 is shown together with a full length housing 21 and balloon 40. An adapter 50 is shown attached to the catheter to communicate with channel 45 to enable flushing the air out of the channel and inflation of the balloon.

In FIG. 5B the housing 21 extends only along a fraction of the length of the catheter. In one embodiment the housing and dilitation balloon extend about 25 centimeters back from the distal aspect of the catheter. This embodiment offers two advantages relative to conventional catheters. First, it eliminates the need for exchange wires which tend to be particularly cumbersome. Second, this embodiment allows for extracorporeal fixation of the intracoronary guidewire during manipulation of the catheter within the heart because both extracorporeal elements are independent. Fixation of the guidewire minimizes motion of the wire within the coronary artery as the angioplasty dilitation balloon catheter is advanced within the heart and thus minimizes some of the intra-arterial trauma that develops as a result of the inadvertent guidewire movement. This embodiment also eliminates the need for a second angiographer to stabilize the guidewire during this aspect of an angioplasty.

In the embodiment of FIG. 5C the only aspect of the catheter that encompasses the guidewire is the balloon itself. The midportion of the catheter of this embodiment simply consists of one or more adjacent or coaxially disposed channels 45 extending from the flush/infusion fitting 50 to the balloon 40. Although the least stable configuration of the three, this embodiment affords the smallest caliber for the angioplasty dilitation balloon catheter. This permits the introduction of this catheter within a guiding catheter of proportionately smaller caliber. The use of a smaller guiding catheter allows the performance of a smaller arteriotomy, permitting the performance of a percutaneous dilitation procedure with minimal risk for peripheral vascular complications and hemorrhage. This design also permits complete separation of the catheter from the guidewire, following inflation of the balloon, substantially minimizing the likelihood of dislodging the guidewire during subsequent withdrawal of the deflated dilitation catheter.

The catheter system of my invention offers several advantages over both the Hartzler system and conventional low profile catheter systems. The deflated cross-sectional profile of my catheter is substantially smaller than the corresponding profile of all currently available catheter systems. By eliminating the tubing that constitutes the housing for the guidewire within the confines of the balloon at the distal aspect of the catheter, a considerable amount of the bulk that contributes to the deflated cross-sectional profile of the catheter is eliminated. Also eliminated is the need to attach the deflated (and hence planar) balloon to the circumference of the tubing, a geometrical incongruity that frequently leads to the development of wrinkles. The wrinkles contribute to the deflated cross-sectional profile of all currently available low profile angioplasty dilitation balloon catheters. The wrapped configuration provides a means of disposing a dilitation balloon of larger caliber when inflated than corresponding prior art low profile catheters. This feature allows an operator, using this device, to introduce a dilitation balloon, of optimal (inflated) caliber, across a stenosis at the outset, with relative facility, without resorting to the installation and inflation of additional dilitation balloon catheters of sequentially larger caliber.

By reducing the length of the guidewire housing, the need to use long and frequently cumbersome exchange wires, the installation of which requires the participation of two operators, is eliminated. It should be recognized that an exchange wire is simply a guidewire that is twice the length of a regular intracoronary guidewire. The additional length the wire is used during the exchange of conventional prior art dilitation catheters. Thus, the wire must extend from the heart to the distal aspect of an angioplasty dilitation catheter when the catheter has been fully removed from the body.

Figure 6A:
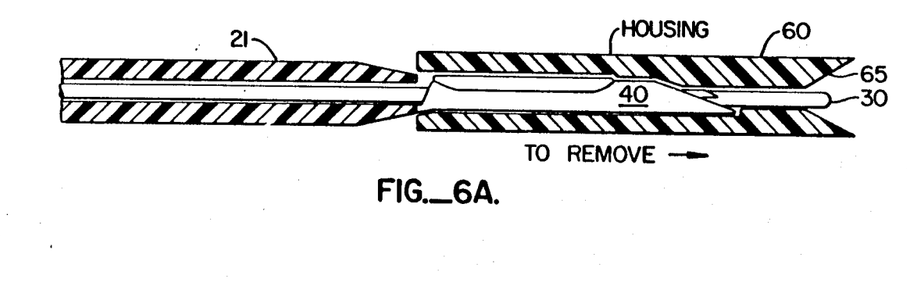
FIGS. 6A and 6B illustrate a removable protective cover for the dilitation balloon designed to prevent unwrapping of the dilitation balloon during flushing and preparation of the catheter for introduction into the body.
Figure 6B:
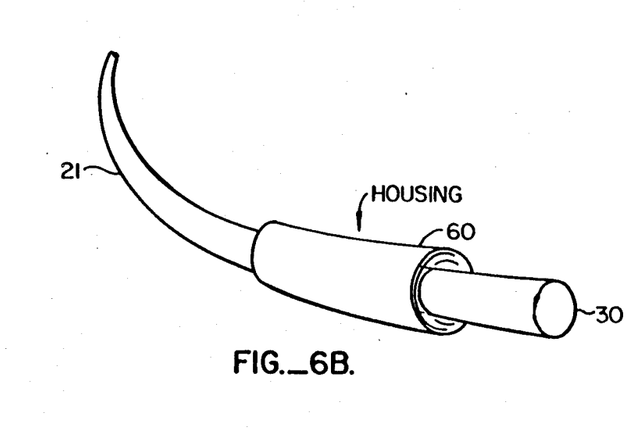
Figures 7A, 7B:
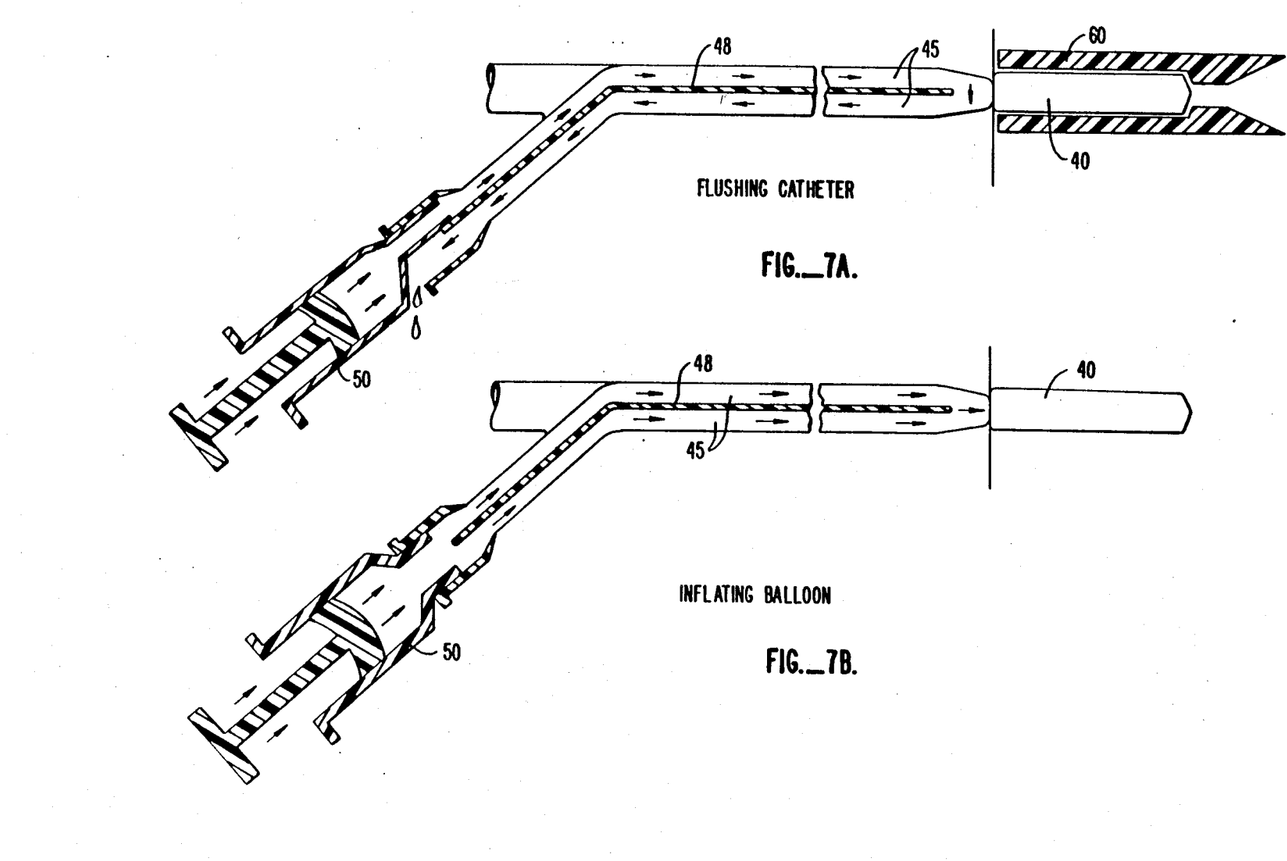
FIG. 7A illustrates the use of a flushing syringe for flushing the channels of a dual lumen catheter.
FIG. 7B illustrates the use of an inflating syringe with the dual lumen catheter of FIG. 7A.

FIG. 6A illustrates in cross section a cover 60 adapted to fit over the wrapped balloon 40 and guidewire 30. Cover 60 protects the balloon 40 during shipment and facilitates preparation of the catheter by providing a cone-shaped surface 65 for threading the guidewire 30 into housing 21. As will be described in conjunction with FIG. 7, the cover also facilitates flushing of the catheter. FIG. 6B is a perspective view showing the cover 60 encompassing the balloon following introduction of the guidewire into the catheter lumen.

The preparation of a conventional catheter involves the flushing of the system with Renograffin-76, a conventional radiographic contrast agent diluted with normal saline. This flushing is to eliminate any air bubbles that might be trapped within the system. This procedure results in full inflation of the angioplasty dilitation balloon before it is ever introduced within the body. Clearly, in the case of the catheter of my invention, this approach would be counterproductive because premature inflation of the balloon results in disruption of the bond which maintains the wrapped configuration of the balloon and unwraps the balloon itself from the guidewire. To avoid this, the catheter is distributed with a protective cover, similar to the protective cover 60 shown in FIG. 7A, in place. The housing prevents inflation of the balloon during the flushing procedure. Because the balloon is tightly wrapped at the outset, it will not contain air. Hence, to adequately prepare the catheter described herein for introduction into the body, it remains necessary only to flush the air out of channel(s) 45, and this can be accomplished by means of a venting system illustrated in FIG. 7A. Cover 60 then is removed prior to insertion of the catheter.

With respect to flushing of catheters in general, there exist three different approaches. Preparation of systems that contain no venting system depend upon the brute force of the operator to generate a substantial vacuum within the system prior to the introduction of any fluid. Preparation of these systems is frequently time consuming, awkward and invariably results in the introduction of some air into the system. Low profile systems are commonly constructed without a venting system.

A second approach to flushing involved the introduction of a venting tube (contained within the dilitation catheter) within the confines of the balloon to vent the system. Once the catheter has been vented, the tube is withdrawn and closed. This approach is time-consuming and cumbersome. Furthermore, the vent tube contributes to the cross-sectional profile of the catheter as well as the dead space of the system, once the catheter has been flushed.

The third and clearly superior approach involves catheter that contains two lumens, in addition to the lumen for the guidewire. Such a catheter is depicted in FIGS. 7A and 7B. At the outset one of the lumens functions as a flush port and one functions as a vent port for the system. Once the catheter has been flushed, the extracorporeal vent is eliminated and the vent port is converted to an additional flush port. This approach offers several advantages. The system provides a vent for the catheter, thus minimizing both the amount of air trapped in the system, as well as the amount of force required to prepare the system. The configuration does not entail any dead space. Also, once the system has been flushed, both channels function to inflate and deflate the balloon. Because the resistance incurred during the inflation and deflation of the dilitation balloon is proportional to the cross-sectional profile of the infusion channel(s), the use of two channels allows the operator to inflate and deflate the balloon more rapidly relative to a single channel (and hence, smaller caliber) flush port system.

The partition 48 separating the flush channel from the vent channel does not extend the entire length of the flush/vent port. To flush the system, one need only insert a preshaped syringe into only the flush port and inject fluid. In this circumstance, the vent port is open to air. Once the vent port has filled with fluid, the catheter is fully flushed. The preshaped syringe is removed and the catheter attached to a standard inflation device, typically a syringe. Because the coupling of the inflation device does not extend deep within the lumen of the flush/vent port, both channels are exposed to hydrostatic pressure on inflation of the balloon and hence, both channels function as flush channels.

I claim:

1. A catheter comprising:
   a guidewire extending from a proximal end to a distal end;
   an inflatable dilitation balloon having a wall defining the interior of the balloon and with at least a portion of said balloon wrapped around a portion of the guidewire proximate the distal end of the guidewire without any portion of said guidewire being in said interior of said balloon; and
   means for inflating the balloon.

2. A catheter as in claim 1 further comprising means for securing the balloon wrapped around the guidewire to enable insertion into a vessel.

3. A catheter as in claim 2 wherein the balloon comprises an inflatable elongate member having a generally tapered shape attached along at least a portion of its exterior length to the guidewire.

4. A catheter as in claim 2 wherein the means for securing comprises means for securing a first region of the balloon to a second region of the balloon to thereby maintain the balloon wrapped around the guidewire.

5. A catheter comprising:
   an inflatable dilitation balloon with at least a first region of said balloon positioned adjacent a second region to define a lumen of a size to accommodate a guidewire;
   means for inflating said balloon; and
   means for providing a temporary bond between the first and second regions, which bond breaks when the balloon is inflated.

6. A catheter as in claim 1 wherein the means for inflating comprises longitudinal channel means extending from the balloon toward the proximal end of the guidewire, the channel communicating with the balloon.

7. A catheter as in claim 1 wherein the longitudinal channel means comprises at least two channels extending from the balloon toward the proximal end of the guidewire.

8. A catheter as in claim 1 further comprising an elongate housing adapted to be inserted into a vessel through which housing the guidewire extends.

9. A catheter comprising:
   an inflatable dilitation balloon with at least a first region of said balloon positioned adjacent a second region to define a lumen;
   means for inflating said balloon;
   an elongate housing adapted to be inserted into a vessel, said balloon being attached to the distal end of said housing; and
   wherein the housing includes a longitudinal slot extending from a distal end thereof.

10. A catheter as in claim 8 wherein the elongate housing extends from the proximal to the distal end of the catheter.

11. A catheter as in claim 8 wherein the elongate housing extends from the distal end of the catheter a selected distance.

12. A catheter as in claim 1 further comprising a cover adapted to cover the dilitation balloon and at least a portion of the distal end of the guidewire.

13. A catheter as in claim 1, further comprising a cover adapted to cover the dilitation balloon, wherein the cover surrounds the dilitation balloon to prevent it from inflating.

14. A catheter as in claim 13 wherein the cover comprises an elongate body having an opening therethrough within which the dilitation balloon is disposed.

15. A catheter, as claimed in claim 4, wherein said means for securing comprises at least a first ultrasonic weld between part of said first region of the balloon and part of said second region of the balloon.

16. A catheter, as claimed in claim 5, wherein said means for providing a temporary bond comprises an ultrasonic weld between at least parts of the first and second regions.

17. A catheter, as claimed in claim 9, further comprising means for providing a temporary bond between parts of said first and second regions of said balloon, which bond breaks when the balloon is inflated.

18. A catheter, as claimed in claim 17, wherein said means for providing a temporary bond comprises an ultrasonic weld between parts of said first region and said second region.

19. A catheter, as claimed in claim 1, further comprising stiffener means attached to said wall of said balloon.

20. A catheter, as claimed in claim 5, further comprising stiffener means attached to a wall of said balloon.

21. A catheter, as claimed in claim 9, further comprising stiffener means attached to a wall of said balloon.

22. A catheter, as claimed in claim 1, further comprising a deformable stint adjacent to said balloon.

23. A catheter, as claimed in claim 5, further comprising a deformable stint adjacent to said balloon.

24. A catheter, as claimed in claim 9, further comprising a deformable stint adjacent to said balloon.

25. A catheter, comprising:
a guidewire extending from a proximal end to a distal end; and
a dilitation balloon inflatable from a first uninflated configuration to a second inflated configuration, wherein at least a portion of said balloon is wrapped around a portion of said guidewire when said balloon is in said uninflated condition, and wherein said guidewire and said balloon part when said balloon is in said inflated condition, such that said guidewire is substantially not surrounded by said balloon.

26. A catheter, comprising:
a guidewire extending from a proximal end to a distal end;
a dilitation balloon inflatable from a first uninflated configuration to a second inflated configuration, said balloon having a wall defining the interior of the balloon;
at least a portion of said balloon in said uninflated condition wrapped around a portion of the guidewire proximate the distal end of the guidewire;
means for inflating the balloon;
means for securing a first region of the balloon to a second region of the balloon by ultrasonic welding to maintain the balloon wrapped around the guidewire when said balloon is in said uninflated condition, wherein said ultrasonic weld breaks when said balloon is inflated to said inflated condition;
an elongate housing adapted to be inserted into a vessel through which housing the guidewire extends, said elongate housing having a longitudinal slot extending from a distal end thereof;
said elongate housing defining a first and a second channel extending from the balloon toward the proximal end of the guidewire, said first channel for flushing said catheter, and said second channel usable for venting and for flushing said catheter; and
a cover comprising an elongate body having an opening therethrough within which the dilitation balloon is disposed to prevent the balloon from inflating.

27. A catheter, comprising:
an elongate housing adapted to be inserted into a vessel, said housing defining a lumen having a first diameter and having a proximal end and a distal end;
a dilitation balloon having a wall defining the interior of the balloon, the wall having an exterior surface and an interior surface, the balloon being inflatable from a first uninflated configuration to a second inflated configuration attached proximate the distal end of the housing;
means for inflating the balloon;
said balloon wall exterior surface, while said balloon is in said uninflated condition, defining a lumen of a size to accommodate a guidewire and substantially coaxial with said housing lumen.

28. A catheter, as claimed in claim 27, wherein said balloon in said uninflated condition has a diameter greater than said diameter of said housing lumen.

29. A catheter, comprising:
an elongate housing adapted to be inserted into a vessel, defining a lumen with a first diameter;
a dilitation balloon attached to the distal end of the housing, said balloon being inflatable from a first uninflated condition to a second inflated condition;
said balloon in said uninflated condition with at least a first region of said balloon positioned adjacent a second region to define a balloon lumen having a second diameter less than said first diameter; and
a guidewire having a proximal end and a distal end, a portion of said guidewire tapering in a direction toward said distal end, a portion of said guidewire disposed in said housing lumen, at least a part of said tapered portion of said guidewire disposed in said balloon lumen.

30. A catheter, comprising:
a guidewire extending from a proximal end to a distal end;
an inflatable dilitation balloon with at least a portion of said balloon wrapped around a portion of the guidewire proximate the distal end of the guidewire;
stiffening means attached to said balloon and spaced from said guidewire; and
means for inflating the balloon.

31. A catheter, comprising:
an elongate housing having a distal end and a proximate end, adapted to be inserted into a vessel;
an inflatable dilitation balloon attached to said distal end of said housing with at least a first region of said balloon positioned adjacent said second region to define a lumen of a size to accommodate a guidewire;

first channel means in said housing for flushing said catheter; and second channel means in said housing for venting said catheter, wherein said second channel means is configurable as a second means for flushing.

32. A method for inflating a balloon of a catheter, comprising:

providing a guidewire extending from a proximal to a distal end;

providing an inflatable dilitation balloon having a wall defining the interior of the balloon with at least a portion of said balloon wrapped around a portion of the guidewire proximate the distal end of the guidewire;

providing flushable channel means in fluid communication with said interior of said balloon; and flushing said flushable channel means to inflate said inflatable balloon to an inflated condition, wherein substantially no portion of said guidewire is in said interior of said balloon.

33. A catheter, as claimed in claim 13, wherein said cover includes a cone-shaped surface for threading the guidewire.

* * * * *